US010054587B2

(12) United States Patent
Huet et al.

(10) Patent No.: US 10,054,587 B2
(45) Date of Patent: Aug. 21, 2018

(54) METHOD FOR DETERMINING THE LEVEL OF AGGLUTINATION OF PARTICLES IN A SAMPLE

(71) Applicant: Commissariat a L'Energie Atomique et aux Energies Alternatives, Paris (FR)

(72) Inventors: Maxime Huet, Grenoble (FR); Jean-Guillaume Coutard, Saint-Pancrasse (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 144 days.

(21) Appl. No.: 15/086,694

(22) Filed: Mar. 31, 2016

(65) Prior Publication Data

US 2016/0291015 A1   Oct. 6, 2016

(30) Foreign Application Priority Data

Mar. 31, 2015   (FR) ...................................... 15 52715

(51) Int. Cl.
| | | |
|---|---|---|
| *G06K 9/00* | (2006.01) | |
| *G01N 33/569* | (2006.01) | |
| *G01N 15/00* | (2006.01) | |
| *G01N 33/49* | (2006.01) | |
| *G01N 33/53* | (2006.01) | |
| *G01N 15/14* | (2006.01) | |

(52) U.S. Cl.
CPC ....... *G01N 33/56966* (2013.01); *G01N 15/00* (2013.01); *G01N 33/4905* (2013.01); *G01N 33/5304* (2013.01); *G01N 15/1468* (2013.01); *G01N 2015/0092* (2013.01)

(58) Field of Classification Search
CPC .............. G01N 15/00; G01N 15/1468; G01N 33/4905; G01N 33/5304; G01N 33/56966; G01N 2015/0092
See application file for complete search history.

(56) References Cited

U.S. PATENT DOCUMENTS

| | | | | |
|---|---|---|---|---|
| 5,594,808 A | * | 1/1997 | Shen ...................... | G01N 21/82 |
| | | | | 356/39 |
| 5,768,407 A | * | 6/1998 | Shen ...................... | G01N 21/82 |
| | | | | 356/39 |

(Continued)

FOREIGN PATENT DOCUMENTS

| | | |
|---|---|---|
| EP | 0 637 744 A1 | 2/1995 |
| EP | 0 822 412 A1 | 2/1998 |

(Continued)

OTHER PUBLICATIONS

French Preliminary Search Report dated Nov. 10, 2015 in French Application 15 52715, filed Mar. 31, 2015 (with English Translation of Categories of Cited Documents).

*Primary Examiner* — Shefali Goradia
(74) *Attorney, Agent, or Firm* — Oblon, McClelland, Maier & Neustadt, L.L.P.

(57) ABSTRACT

The invention relates to a method for quantifying the level of agglutination of particles in a sample, in particular a biological sample, and notably blood. The biological sample is positioned between a light source and a matrix photodetector. The image acquired by the photodetector is representative of the level of agglutination of the particles in the sample. The light source emits a light wave, the spectral band of which extends an optimum 400 and 600 nm, which constitutes an optimum an excessively low absorption and excessively high absorption, given the thickness of the sample.

13 Claims, 4 Drawing Sheets

(56) References Cited

U.S. PATENT DOCUMENTS

| | | | |
|---|---|---|---|
| 6,030,845 A | 2/2000 | Yamao et al. | |
| 8,417,002 B2* | 4/2013 | Batistoni | G01N 21/82 382/128 |
| 2003/0082662 A1 | 5/2003 | Nakashima et al. | |
| 2006/0106316 A1* | 5/2006 | Palti | A61B 1/041 600/476 |
| 2009/0191641 A1* | 7/2009 | Chiapperi | B01L 3/5025 436/69 |
| 2009/0274348 A1* | 11/2009 | Jakubowicz | G01N 33/5304 382/128 |
| 2011/0104738 A1 | 5/2011 | Forsell et al. | |
| 2013/0323757 A1 | 12/2013 | Poher et al. | |

FOREIGN PATENT DOCUMENTS

| | | |
|---|---|---|
| EP | 1 027 932 A2 | 8/2000 |
| EP | 2 775 292 A1 | 9/2014 |

\* cited by examiner

METHOD FOR DETERMINING THE LEVEL OF AGGLUTINATION OF PARTICLES IN A SAMPLE

TECHNICAL FIELD

The invention relates to a method for determining a level of agglutination of particles in a sample, and in particular an agglutination of cells, notably of blood cells, using an optical device. The method can be implemented for medical diagnostic purposes.

PRIOR ART

The use of optical methods for observing the agglutination of cells in a fluid, and for deriving quantitative information therefrom, for example for diagnostic purposes, is a recent development.

The European patent EP2669678 describes a process making it possible to determine a state of agglutination of particles, and notably of red blood cells, by positioning a sample, including the particles, between a light source and a matrix photodetector. The sample includes a reagent suitable for promoting the agglutination of the red blood cells. The red blood cells are illuminated by the light source and generate, on the matrix photodetector, an image representative of their state of agglutination. More specifically, as the red blood cells agglutinate, the morphology of the detected image evolves. Thus, through an image analysis, it is possible to track the trend of the agglutination of the red blood cells in the sample. It is also possible to establish quantative indicators characterizing the state of agglutination, that is to say the quantity of red blood cells agglutinated in the sample.

This method proves particularly effective for producing reliable analyses using a simple and inexpensive means, that can for example be incorporated in a portable device, called "point of care", meaning "at the bedside of the patient". It makes it possible, for example, to perform a blood grouping or a dosage of analyte present in the sample notably by introducing a bispecific reagent therein, the bispecific reagent being able to bond jointly with the analyte and with a red corpuscle. Thus, when the quantity of bispecific reagent introduced into the sample is controlled, the formation of agglutinates of red blood cells depends on the concentration of said analyte in the sample. The determination of an indicator quantifying the agglutination allows for a dosage of the concentration of the analyte.

The inventors have brought a refinement to this method, particularly by improving its sensitivity.

SUMMARY OF THE INVENTION

One subject of the invention is a method for determining a level of agglutination in a sample, the sample including particles, said particles being able to agglutinate so as to form one or a plurality of agglutinates in said sample, the method comprising the following steps:
  illuminating said sample using a light source, the light source producing an incident light wave, that is propagated towards the sample along a propagation axis
  acquiring, using a matrix photodetector, an image of the sample, the sample being positioned between said light source and said matrix photodetector;
  determining a level of agglutination of particles in the sample, using said image;
characterized in that:
  said incident light wave exhibits a spectral band centred on a wavelength less than 600 nm.

In one embodiment, the particles can be red blood cells. In one embodiment, the samples includes a bodily fluid, for example blood.

According to an embodiment, the spectral band is centred on a wavelength range of between 400 nm and 600 nm. The width of the spectral band may be less than 200 nm and preferably less than 100 nm.

According to an embodiment, the thickness of the sample, along the propagation axis, can notably be less than 1 cm, even less than 5 mm, even, and in particular when the sample is whole blood, less than 1 mm, even less than 500 µm.

According to an embodiment, the spectral band is preferably centred on a wavelength, called central wavelength, of between 400 nm and 600 nm. Preferably, said spectral band extends neither above 600 nm nor below 400 nm.

Preferably, the width of said spectral band is less than 100 nm, and preferably less than 50 nm, even less than 25 nm.

In one embodiment, the step of determining the level of agglutination comprises:
  i) selecting, in said image, dark zones, the intensity of which is below a first threshold and/or of light zones, the intensity of which is above a second threshold;
  ii) determining a statistical indicator representative of said selected zones;
  iii) determining a level of agglutination as a function of the value of said statistical indicator.

In one embodiment, prior to acquiring said image, the method includes a step of adding a reagent into the sample, suitable for generating the agglutination of said particles.

According to an embodiment, the method comprises a step of dosage of analyte present in the sample as a function of the estimated level of agglutination.

According to an embodiment, the sample comprises blood and the method comprises a step of determination of a blood group as a function of the estimated level of agglutination.

Another subject of the invention is a device for determining a level of agglutination in a sample, the sample including particles, said particles being able to agglutinate so as to form one or a plurality of agglutinates in said sample, the device comprising:
  a light source arranged to produce an incident light wave, along a propagation axis, towards said sample;
  a support, configured to hold the sample between said light source and a matrix photodetector;
  the matrix photodetector, being arranged to acquire an image of the light wave transmitted by the sample, when the latter is exposed to said incident light wave;
  a processor, suitable for determining a level of agglutination of the particles in the sample as a function of said image;
the device being characterized in that:
  the light source configured such that said incident light wave exhibits a spectral band centred on a wavelength less than 600 nm.

Level of agglutination should be understood to mean a value representative of a quantity of particles agglutinated in the sample.

FIGURES

DESCRIPTION OF PARTICULAR EMBODIMENTS

Figure 1:
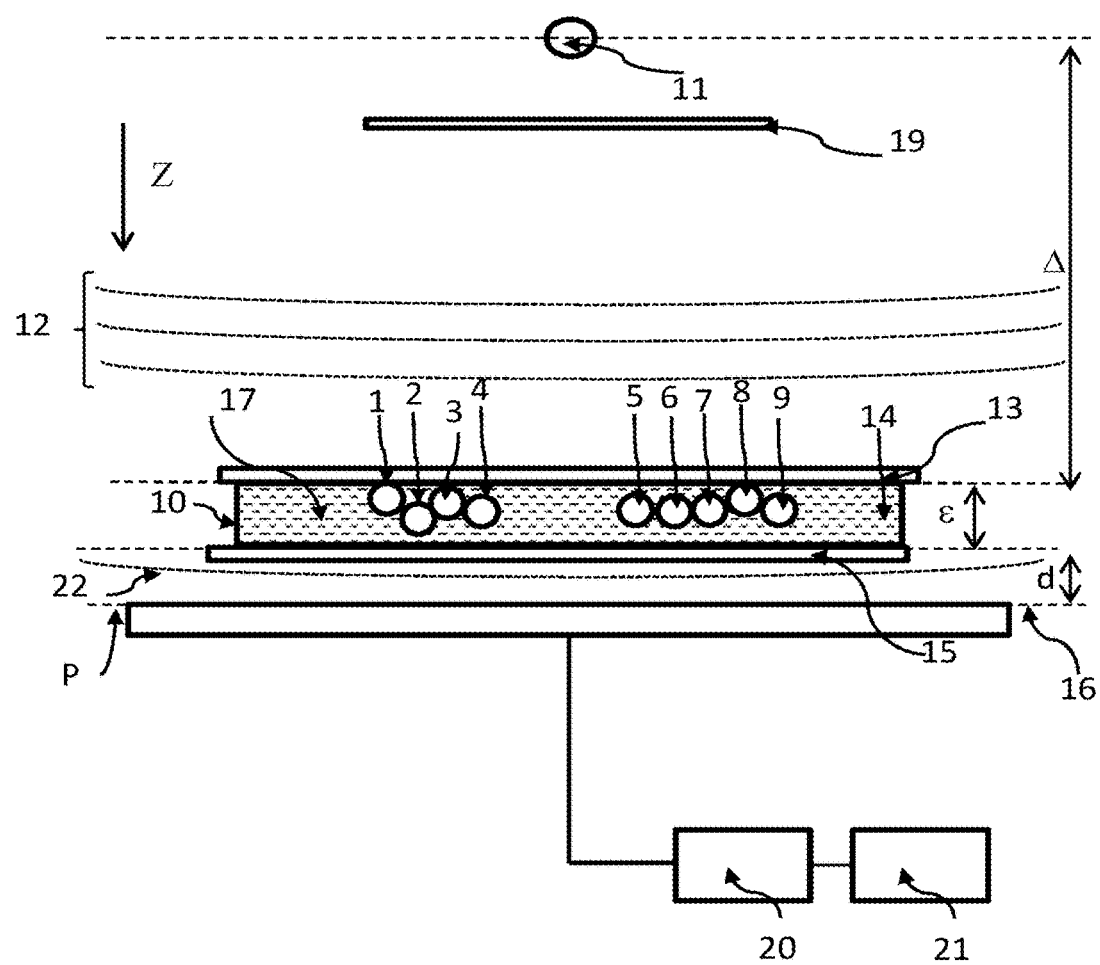
FIG. 1 represents an exemplary device according to the invention.

FIG. 1 represents an exemplary device that is the subject of the invention. A light source 11 is able to produce a light wave 12, called incident light wave, towards a sample 10, along a propagation axis Z.

The sample 10 comprises a medium 14 and particles 1, 2, ... 9 soaking in this medium.

The medium 14 can notably comprise a fluid, in particular a bodily fluid, for example blood. It can notably be whole blood. The particles 1, 2 ... 9 can be blood particles, and more particularly red blood cells.

The distance Δ between the light source and the sample 10 is preferably greater than 1 cm. It preferably lies between 1 and 30 cm, typically 5 cm.

Preferably, the light source, seen by the sample 10, is considered to be in the form of a spot, but this is not essential. The term in the form of a spot describes the fact that its diameter (or its diagonal) must be less than a fifth, better, a tenth of the distance between the sample and the light source. Thus, the light reaches the sample 10 in the form of planar waves, or waves that can be considered as such.

The light source 11 can be associated with a diaphragm 18 so as to appear in the form of a spot. The aperture of the diaphragm is typically between 50 μm and 1 mm, preferably between 50 μm and 500 μm.

The light source 11 can also be fibred. In this case, an optical fibre extends between a first end, positioned facing a light source, and collecting the light therefrom, and a second end, emitting the light towards the sample 10. In this case, this second end is considered to be the light source 11.

The sample 10 is supported by an enclosure, comprising a bottom 15 and a cover 13. The side walls of the enclosure are not represented. Typically an enclosure is a fluidic chamber, into which the sample 10 is introduced, for example by capillarity. In the example considered, the bottom 15 and the cover 13 consist of two transparent plates 100 μm apart. The distance between the bottom 15 and the cover 13, along the propagation axis Z, corresponds to the thickness 8 of the sample. The latter varies typically between 20 μm and 1 cm, and is preferably between 50 μm and 500 μm, for example 150 μm.

The sample 10 is positioned between the light source 11 and a matrix photodetector 16, suitable for establishing an image I. The matrix photodetector extends along a detection plane P, preferably parallel, or substantially parallel to the bottom 15 of the enclosure delimiting the sample. The term substantially parallel means that the two elements need not be strictly parallel, an angular tolerance of a few degrees, less than 20° or 10°, being accepted.

The light source 11 may be temporally coherent but this is not necessary. In effect, a coherent light source like a laser diode may induce a diffraction phenomenon on dust or scratches, located on the path of the light, between the source 11 and the matrix photodetector 16. These diffraction effects, generated by exogenous diffracting elements, not forming part of the sample, can induce a noise in the image I formed by the photodetector 16. This is why the inventors consider that a source that is not temporally coherent, such as a light-emitting diode, or LED, is preferable.

A filter 19 can be positioned between the light source and the sample, so as to block the wavelengths outside of a predetermined pass band. The use of such a filter is detailed hereinbelow. Thus, the incident light wave 12 at the sample 10 extends according to a spectral band that is reduced in relation to the spectral band emitted by the light source 11.

The matrix photodetector 16 is an image sensor comprising a matrix of pixels, of CCD (charge coupled device) type, or of CMOS (complementary metal-oxide semiconductor). The CMOS photodetectors are preferred because the size of the pixels is smaller, which makes it possible to acquire images with a more favourable spatial resolution.

Preferably, the matrix photodetector comprises a matrix of pixels, above which is positioned a transparent protection window. The distance between the matrix of pixels and the protection window is generally between a few tens of μm and 150 to 200 μm. Preferably, the detection plane P along which the matrix photodetector extends is at right angles to the propagation axis Z of the incident light wave (12).

Generally, and regardless of the embodiment, the distance d between the sample 10 and the pixels of the photodetector 16 is less than 2 cm, even less than 1 cm, and preferably lies between 50 μm and 2 cm, preferably between 100 μm and 2 mm.

The matrix photodetectors for which the pitch between pixels is less than 3 μm are preferred because they make it possible to obtain images with a satisfactory spatial resolution.

The absence of magnifying optics between the matrix photodetector 16 and the sample 10 will be noted. This does not prevent the possible presence of focusing microlenses on each pixel of the photodetector 16.

The matrix photodetector is able to produce an image I of a light wave 22 transmitted by the sample 10 when the latter is illuminated by the light source 11. The image I is acquired with all or a part of the wavelengths produced by the light source. This light wave 22 results from the interaction of the particles present in the sample with the incident light wave 12, produced by the light source 11. In effect, under the effect of the incident light wave, a particle of the sample can generate a diffracted wave, likely to produce an interference with the incident wave 12 passing through the sample. The interference between the wave diffracted by the particle and the incident light wave 12 gives rise, on the image acquired by the photodetector, to an elementary diffraction figure, comprising a central zone and a number of concentric diffraction rings.

Moreover, the particles present in the sample can be agglutinated, spontaneously or under the effect of a reagent 17 added to the sample. In such a case, the agglutinates formed absorb a part of the incident light wave 12.

Thus, the light wave 22 to which the matrix photodetector is exposed can comprise:

A component resulting from the diffraction of particles present in the sample, under the effect of the incident light wave 12, this diffraction component being reflected by the presence of elementary diffraction figures on the photodetector, each elementary diffraction figure being associated with a diffracting particle.

A component resulting from the absorption of the incident light wave in the sample, this absorption component being reflected in a reduction of the light intensity on the matrix photodetector 16.

A processor 20, for example a microprocessor, is able to process the images I generated by the matrix photodetector 16. In particular the processor is a microprocessor linked to a programmable memory 21 in which is stored a sequence of instructions for performing the image processing and computation operations described in this description. These instructions can be run by the processor 20.

This device is similar to that described in the European patent EP2669678, previously cited. However, the examples described therein mention the use of a light source with an emission spectral band centred on the wavelength λ=670 nm. In effect, it is known that the absorption spectrum of blood, and in particular of oxyhaemoglobin, exhibits a plateau beyond 600 nm, the absorption being particularly weak in a spectral band lying between 600 nm and 900 nm, i.e. within the red or near-infrared range.

Because of this, in the examples described in the above-mentioned European patent, the component deriving from the diffraction of the particles is probably predominant, because of the use of a light source with an emission wavelength towards which the absorption of the blood is low.

Figure 2:
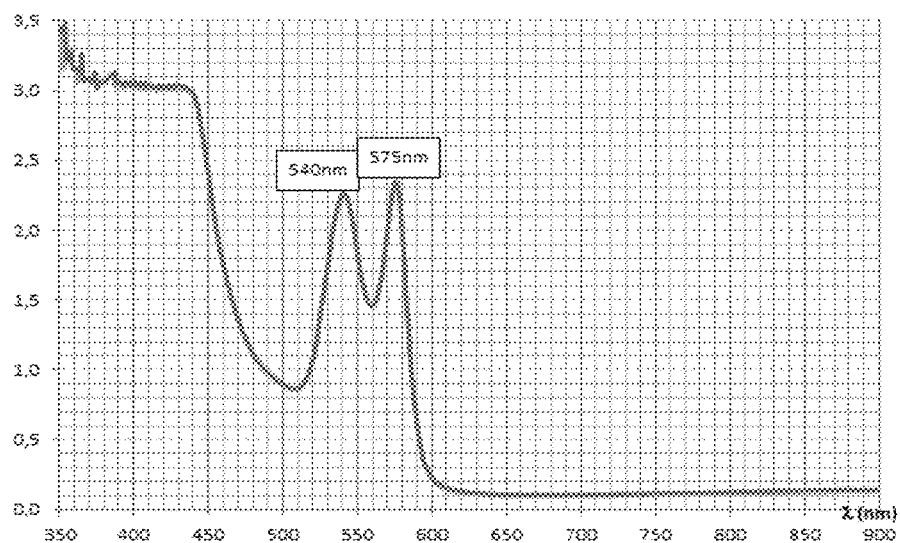
FIG. 2 represents a curve showing the absorption of a blood sample as function of the wavelength.

FIG. 2 represents the absorption spectrum of a sample composed of whole blood to which a saponin concentration of 25 mg/ml has been added, the sample being positioned in a transparent fluidic chamber with a thickness ε equal to 150 μm. The x axis represents the wavelength, whereas the y axis represents the measured absorption.

As is known, the addition of saponin leads to the lysis of the red blood cells in the sample, referred to by the term haemolysis. This makes it possible to limit the effect of the diffusion of the light by the red blood cells on the measurement. These measurements were performed according to a configuration similar to that represented in FIG. 1, by illuminating the sample using a white light source positioned upstream of a monochrometer, the photodetector being a spectrophotometer. This spectrum corresponds substantially to the absorption spectrum of oxyhaemoglobin, as presented in the literature, with the presence of two characteristic absorption peaks, respectively centred on the wavelengths 540 nm and 575 nm.

Because of this, when the aim is to perform optical measurements on blood, according to a transmission mode configuration, it seems logical to prioritize a wavelength that can be easily transmitted by the sample, that is to say greater than 600 nm, and to do so more particularly when the thickness of the sample is sufficiently small.

The term transmission mode configuration describes the fact that the sample analysed is positioned between the light source and the photodetector, the latter collecting the light signal transmitted by the sample.

However, the inventors, seeking to refine the method that is the subject of the abovementioned patent, have estimated that, to perform measurements representative of the level of agglutination of particles such as red blood cells, it would be possible to consider, and even preferable, to use a light source configured such that the incident light wave 12 on the sample has a wavelength λ less than 600 nm.

In particular, the spectral band of the incident light wave 12 is preferably between 400 nm and 600 nm, or even more preferably between 450 nm and 600 nm, in as much as the thickness ε of the sample allows for a sufficient transmission of the signal.

Thus, generally, when whole blood is concerned, the thickness a of the sample is preferably less than 1 mm, even than 500 μm. The constraint on the thickness ε is less when it is diluted blood, or when the red blood cells concentration is low. In such cases, nevertheless, the thickness ε of the sample is preferably less than 1 cm.

Between 400 nm and 600 nm, the absorption of the incident light beam 12, emitted by the light source 11, is significant, without being in any way excessive.

The following spectral bands are particularly preferred: 450 nm-480 nm; 530 nm-580 nm. In effect, as can be seen in FIG. 2, in these ranges, the value of the absorption of the blood corresponds to a compromise between an excessively high absorption (for example below 440 nm) and an excessively low absorption (beyond 600 nm).

Also, generally, the light source 11 is configured for the spectral band of the incident light wave 12 to be centred on a wavelength $\lambda_{em}$, called central wavelength, less than 600 nm, and preferably ranging between 400 and 600 nm, and even more preferably between 440 and 600 nm, the spectral ranges [450 nm-480 nm] and [530 nm-580 nm] being considered optimal.

Preferably, the spectral band of the incident light wave 12 has a width less than 200 nm or 100 nm, and even more preferably less than 50 nm or, better, 25 nm. The width of the spectral band should be understood to be the width at mid-height of the emission peak.

Preferably, the spectral band of the incident wave 12 extends neither above 600 nm nor below 400 nm, or possibly marginally. Thus, at least 80%, even more than 90%, of the emitted intensity ranges between 400 nm and 600 nm.

This spectral band of the incident light wave 12 is either produced either directly by the light source 11, or by a filter 19 interposed between the light source and the sample 10.

In the absence of agglutination of red blood cells, or when this agglutination is negligible, the incident light wave 12 is essentially absorbed and the optical signal collected at the detector is weak. The image I formed thereby is a dark, homogeneous image, comprising pixels with a grey level with little dispersion.

When the agglutination becomes significant, that is to say when a sufficient quantity of red blood cells are agglutinated, the concentration of red blood cells is no longer homogeneous in the sample. The latter is divided between a depleted part and an enriched part. The enriched part corresponds to zones, called enriched zones, of the sample in which the concentration of red blood cells increases; these are agglutinates. The depleted part corresponds to zones, called depleted zones of the sample, in which the concentration of red blood cells decreases, because of the formation of the agglutinates.

It will then be understood that the illumination of the sample using a beam with a wavelength that is significantly absorbed by the red blood cells gives rise, in the image I formed on the matrix photodetector 16, in:

Dark zones A, the grey level of which is low, each dark zone corresponding to the projection, on the detector, of an enriched zone of the sample, because of the absorption of the incident light beam 12 by the agglutinates.

Light zones B, the grey level of which is high, each light zone corresponding to the projection, on the detector, of a depleted zone of the sample, because of the increased transmission of the incident light beam 12 between the agglutinates.

Thus, the more the quantity of agglutinated red blood cells increases, the more segmentation of the sample, between depleted zones and enriched zones, increases. The image formed by the detector is representative of this segmentation, and appears increasingly contrasted. The number of pixels below a first threshold, called low threshold, increases, because of the absorption of the incident beam by the agglutinates of red blood cells, whereas the number of pixels above a second threshold, called high threshold, above the first threshold, also increases.

Tests were carried out by positioning whole blood in a fluidic chamber of thickness ε equal to 150 μm. A reagent suitable for inducing the agglutination of red blood cells was previously added. This is a reagent Anti-A from a blood-typing kit, marketed by the company Diagast under the reference Groupakit-70888, the dosage being a volume of blood for a volume of reagent.

The light source 11 was positioned at a distance Δ=5 cm from the sample 10, the latter being positioned at a distance d=1 mm from the matrix photodetector 16.

The matrix photodetector 10 implemented is an 8-bit monochrome CMOS sensor comprising 2592×1944 pixels, reference Mightex BTN-B050-U.

In the first test, the light source 11 is a laser diode emitting in a spectral band centred on the wavelength of 850 nm. The image obtained, 30 seconds after the addition of the reagent, is represented in FIG. 4A.

In the second test, the light source 11 is a white light source (Ocean optics halogen light source HL-2000-FHSA). The image obtained, 30 seconds after the addition of the reagent, is represented in FIG. 4B.

Figure 3:
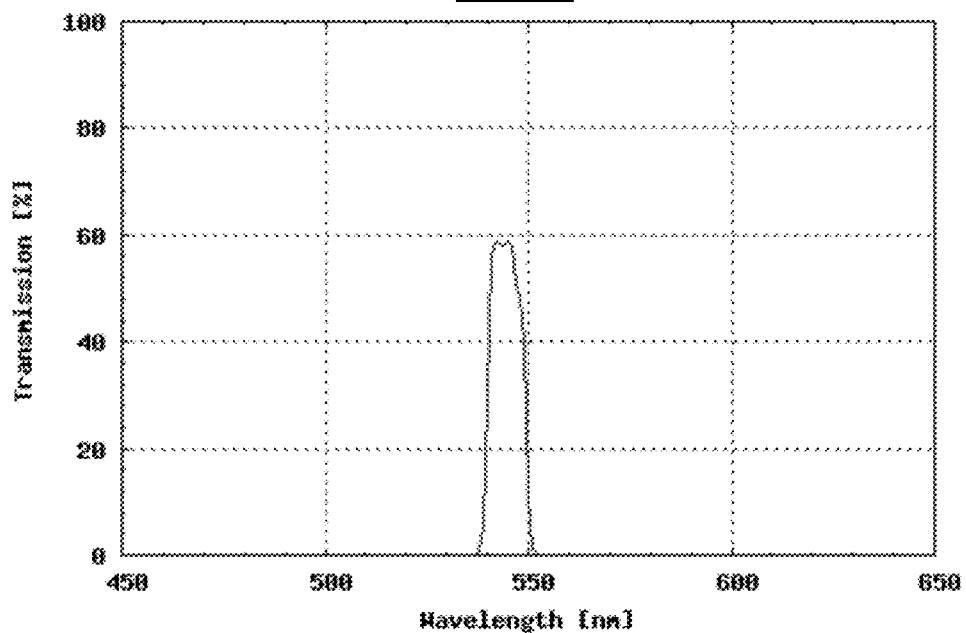
FIG. 3 represents the transmission spectrum of a filter implemented in an exemplary embodiment.

In the third test, the light source 11 is the white light source used in the preceding test, a filter 19 being interposed between the light source and the sample. The objective of the filter is to reduce the emission band of the light source 11, by blocking the wavelengths outside of a predetermined pass band. FIG. 3 represents the transmission function of this filter 19, the reference of which is Omega optical filter XF1020 546DF10. The pass band of this filter is centred on the 546 nm wavelength, and extends substantially between 538 nm and 552 nm. The image obtained, 30 seconds after the addition of the reagent, is represented in FIG. 4C.

Figure 4:
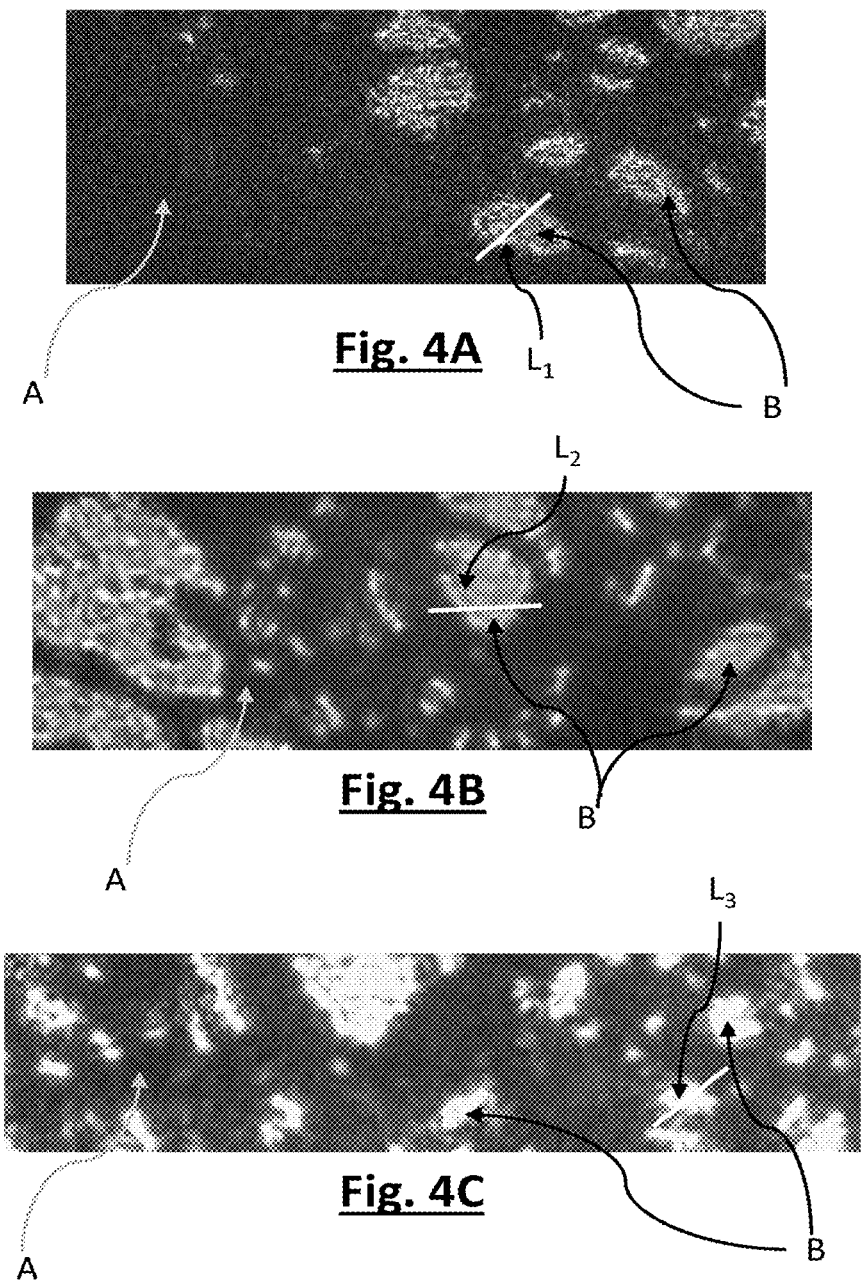
FIGS. 4A, 4B and 4C represent images obtained respectively in three different test configurations.

It will be noted that the three images respectively represented in FIGS. 4A, 4B and 4C correspond to samples 10 that can be considered to be identical: same reagent concentration added, same time since the addition thereof. However, the image 4C appears clearly more contrasted than the image 4B, the latter appearing more contrasted than the image 4A.

A more contrasted image allows for a better distinction between the light zones B and the dark zones A. This makes it possible to better delimit these zones, for example by intensity thresholding, by considering the low thresholds and high thresholds cited previously, or by image segmentation algorithms. A more accurate statistical quantity is thus obtained that makes it possible to quantify the level of agglutination of particles within the sample. The statistical quantity can be:
- a measurement of the spatial extent of the light zones B, zones that group together the pixels with an intensity that is above said high threshold, the spatial extent corresponding to the number of pixels contained in these zones;
- a measurement of the spatial extent of the dark zones A, zones that group together the pixels with an intensity below said low threshold;
- statistical indicators relating to the distribution of the intensity in the light zones B and/or in the dark zones A: average intensity, median intensity, integral of the intensity, variance, etc.

It will be understood that the more contrasted the image is, the more accurately quantified is the level of agglutination of the sample.

Figure 5:
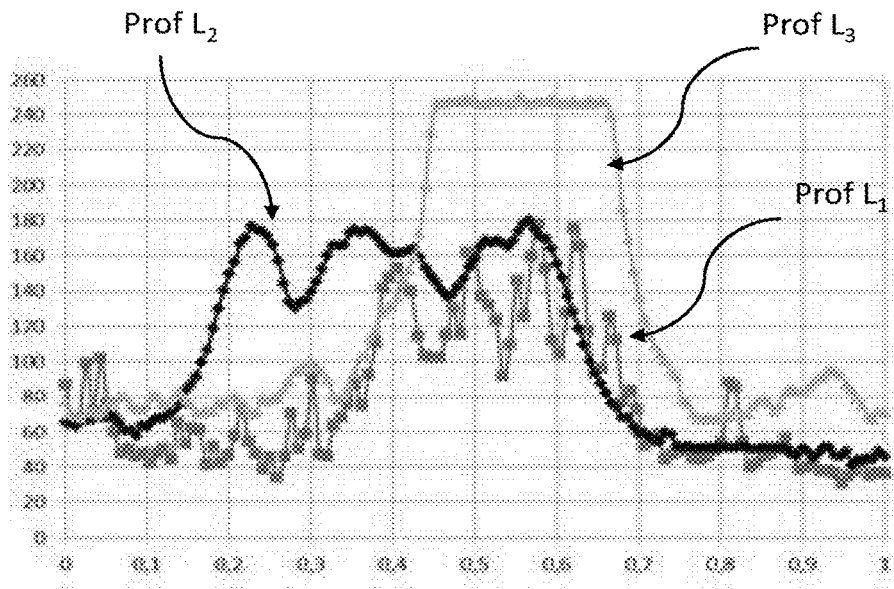
FIG. 5 represents intensity profiles produced on the images 4A, 4B and 4C.

FIG. 5 represents intensity profiles Prof $L_1$, Prof $L_2$ and Prof $L_3$, respectively produced on the lines $L_1$, $L_2$ and $L_3$ respectively represented in FIGS. 4A, 4B and 4C. Each profile was produced on either side of a light zone B, and in said light zone, in order to be able to estimate a signal-to-noise ratio. It will be noted that the contrast-to-noise ratio is clearly more favourable on the profile Prof $L_3$, obtained in the image 4C produced with a filtered white light source 11. The contrast-to-noise ratio corresponding to the profile Prof $L_1$ obtained on the image 4A produced with the laser source centred on λ=850 nm is the lowest.

The term "contrast-to-noise ratio" should be understood to mean the difference between the average intensities of a light zone and B of a dark zone A, divided by the standard deviation of the noise.

It will be understood that the invention represents a notable refinement of configurations in which the wavelength of the light source 11 is greater than 600 nm, and is so on the signal-to-noise ratio. The sensitivity is therefore improved.

Figure 6:
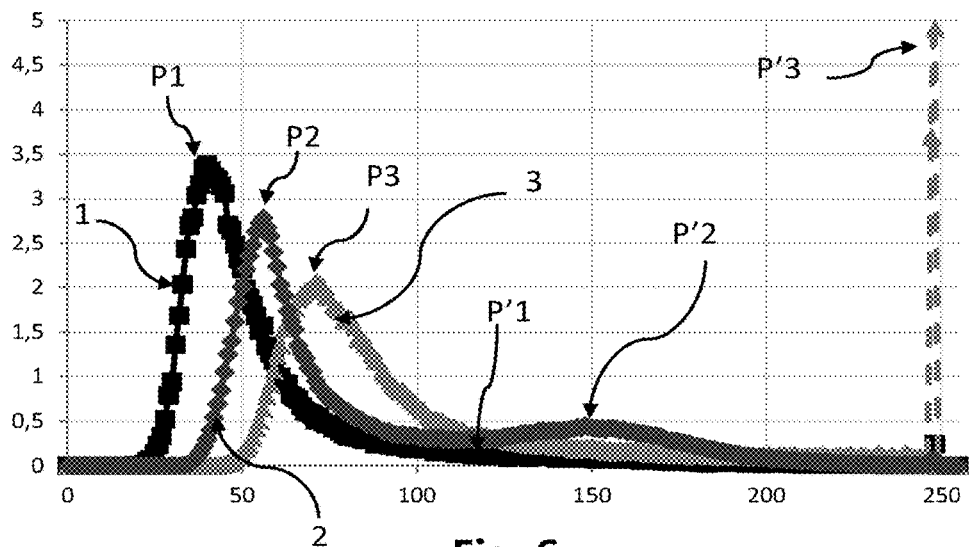
FIG. 6 represents the histograms of the intensity of the pixels of the images represented in FIGS. 4A, 4B and 4C.

FIG. 6 highlights the effect of the light source 11 on the distribution in intensity terms of the pixels of the image formed by the matrix photodetector. This figure represents, for each test, the histogram of intensity of the pixels, the intensity level lying between 0 (minimum grey level—black pixel) and 255 (maximum grey level—white pixel), the dynamic range of the image I being 8 bits.

The histogram corresponding to the first test (laser source, λ=850 nm), bearing the reference 1 in FIG. 6, includes a main peak P1, the maximum value of which corresponds to an intensity level (or grey level) of 40, and extending between the intensity levels 25 and 70. This peak corresponds to the agglutinates, that is to say to the dark zones A of FIG. 4A. A secondary wide peak P'1, of low amplitude, can also be discerned, extending between intensity values lying between approximately 70 and approximately 150, corresponding to the light zones. Note that the bounds of this secondary peak are not clear and are difficult to determine accurately.

The histogram corresponding to the second test (white light source), bearing the reference 2 in FIG. 6, includes a main peak P2 centred on an intensity value of 70, and extending between the intensity values 40 and approximately 75 and a secondary wide peak P'2, centred on an intensity value close to 150, and extending between the intensity values of 120 and 180, these values being indicative because of the spread of this peak. P2 and P'2 correspond respectively to the agglutinates (dark zones A) and to the light zones B. It has to be specified that peak separation algorithms can be applied, culminating in a more accurate delimitation of each peak.

Based on this histogram, the dark zones A and the light zones B of the image 4B can be delimited by considering, respectively, the pixels with an intensity less than 75 (low threshold) and the pixels with an intensity greater than 120 (high threshold). The deviation between the low threshold and the high threshold, expressed as intensity value, amounts to 45.

The secondary peak P'2 is distinguished more easily than the boss P'1, of the preceding test, which testifies to a better contrast of the image produced by using the white light source.

The histogram corresponding to the third test (light source with a spectral range extending between 538 nm and 552 nm), bearing the reference 3 in FIG. 6, includes two clearly delimited sharp peaks P3 and P'3, corresponding respectively to the agglutinates and to the light zones. The peak P3 is maximum at the intensity level of 71, and extends within the intensity range [50-110]. The peak P'3 is maximum at the intensity level 248 and extends over the remarkably narrow intensity range [246-250].

Based on this histogram, the dark zones A and the light zones B of the image 4C can be delimited by respectively considering the pixels with an intensity less than 110 (low threshold) and the pixels with an intensity greater than 246 (high threshold). The deviation between the low threshold and the high threshold, expressed as intensity value, amounts to 113.

The summits of the peaks corresponding respectively to the agglutinates and to the light zones B are more spaced apart when the light source of the third test is used, which testifies to a better contrasted image, allowing for a more accurate quantitative information item as to the state of agglutination of the particles.

The method previously described will be able to be used to characterize the agglutination of particles, and in particular of red blood cells, in a bodily fluid or in a fluid obtained from a bodily fluid. The bodily fluid can be blood, but also other fluids likely to include particles that can agglutinate in particular red blood cells: cerebrospinal fluid, urine, etc.

In the attached drawings the sample 10 is interposed between the light source 11 and the photodetector 16. In an alternative embodiments, the light source 11 and the photodetector 16 can be arranged in the same side with respect to the sample 10. In this case, the sample may preferably be supported by a light reflective surface so as to reflect light back to the matrix photodetector 16.

The particles can be red blood cells, or other cells of comparable optical transmission. There can also be droplets that cannot be mixed with the medium 14, for example lipidic droplets.

The method can be implemented for in the medical diagnostic field, for the dosage of an analyte in a bodily fluid, or for blood group determination applications.

The invention claimed is:

1. A method for determining a level of agglutination in a sample, the sample including particles, said particles being able to agglutinate so as to form one or a plurality of agglutinates in said sample, the method comprising:
    illuminating said sample using a light source, the light source producing an incident light wave, that is propagated towards the sample along a propagation axis;
    acquiring, using a matrix photodetector, an image of the sample, the sample being positioned between said light source and said matrix photodetector;
    determining a level of agglutination of particles in the sample, using said image;
    wherein said incident light wave exhibits a spectral band centred on a wavelength less than 600 nm,
    wherein there is no magnifying lens between the sample and the matrix photodetector.

2. The method according to claim 1, in which the particles are red blood cells.

3. The method according to claim 1 in which the sample includes a bodily fluid.

4. The method according to claim 3, in which the bodily fluid is blood.

5. The method according to claim 1, in which said spectral band is centred on a wavelength of between 400 nm and 600 nm.

6. The method according to claim 1, in which the width of said spectral band is less than 25 nm.

7. The method according to claim 1, in which the sample has a thickness, along said propagation axis, less than 1 cm.

8. The method according to claim 1, in which the determining the level of agglutination comprises:
    i) selecting, in said image, dark zones, the intensity of which is below a first threshold and/or of light zones, the intensity of which is above a second threshold;
    ii) determining a statistical indicator representative of the selected zones;
    iii) determining a level of agglutination as a function of the value of said statistical indicator.

9. The method according to claim 1, comprising, prior to the acquisition of the image, adding a reagent into the sample, suitable for generating the agglutination of the particles within the sample.

10. A device for determining a level of agglutination in a sample, the sample including particles, said particles being able to agglutinate so as to form one or a plurality of agglutinates in said sample, the device comprising:
    a light source arranged to produce an incident light wave, along a propagation axis, towards said sample;
    a support, configured to hold the sample between said light source and a matrix photodetector;
    the matrix photodetector, being arranged to acquire an image of the light wave transmitted by the sample, when the latter is exposed to said incident light wave;
    a processor, configured to receive images from the matrix detector, and further configured to determine a level of agglutination of the particles in the sample as a function of said image;
    wherein the light source is configured such that said incident light wave exhibits a spectral band centred on a wavelength less than 600 nm,
    wherein there is no magnifying lens between the sample and the matrix photodetector.

11. The device according to claim 10, in which said spectral band is centred on a wavelength of between 440 nm and 600 nm.

12. The device according to claim 10, in which the width of said spectral band is less than 25 nm.

13. The device according to claim 10, in which there is no magnifying lens between the support and the matrix photodetector.

* * * * *